(12) United States Patent
Gray

(10) Patent No.: US 12,121,374 B2
(45) Date of Patent: Oct. 22, 2024

(54) CONVERTIBLE CONTAINER

(71) Applicant: Harm Reduction Supplies Corporation, Ontario (CA)

(72) Inventor: Samuel Bradford Gray, Ontario (CA)

(73) Assignee: HARM REDUCTION SUPPLIES, Ontario (CA)

( * ) Notice: Subject to any disclaimer, the term of this patent is extended or adjusted under 35 U.S.C. 154(b) by 0 days.

(21) Appl. No.: 18/146,236

(22) Filed: Dec. 23, 2022

(65) Prior Publication Data

US 2024/0207007 A1    Jun. 27, 2024

(51) Int. Cl.
*A61B 50/36* (2016.01)
*A61B 50/30* (2016.01)

(52) U.S. Cl.
CPC ........ *A61B 50/362* (2016.02); *A61B 50/3001* (2016.02); *A61B 2050/3008* (2016.02); *A61B 2050/3009* (2016.02)

(58) Field of Classification Search
CPC ....... A61B 50/362; A61B 50/20; A61B 50/36; A61B 50/39; A61B 50/37; A61B 2017/00132; A61B 2050/0054; A61J 1/00; A61J 1/14; A61J 1/05; A61J 1/16; B65D 83/0888
USPC ...................... 206/233; 220/495.09, 500, 523
See application file for complete search history.

(56) References Cited

U.S. PATENT DOCUMENTS

| | | | |
|---|---|---|---|
| 4,520,926 A * | 6/1985 | Nelson | A61M 5/3205 206/370 |
| 5,323,902 A | 6/1994 | Palmer et al. | |
| 6,719,017 B1 * | 4/2004 | McArthur | A61B 50/36 141/311 A |
| 7,392,903 B2 | 7/2008 | Jolley et al. | |

FOREIGN PATENT DOCUMENTS

| | | |
|---|---|---|
| CN | 213722479 U | 7/2021 |
| DE | 8708575 U1 | 8/1987 |
| GB | 2530985 | 4/2016 |
| KR | 200384588 Y1 | 5/2005 |

OTHER PUBLICATIONS

Combined Search and Examination Report; issued to GB2319042.4 (Harm Reduction Supplies Corporation on Mar. 20, 2024.

* cited by examiner

*Primary Examiner* — King M Chu
(74) *Attorney, Agent, or Firm* — Jonathan Kidney; Intelink Law Group, P.C.

(57) ABSTRACT

A container for dispensing and disposing supplies is disclosed. The container includes a receptacle having a base and a plurality of walls extended up from the base; one or more compartments formed in the receptacle, wherein the one or more compartments is configured to be fluid-tightly sealed from each other; and one or more insert members, each configured to convert one of the one or more compartments from exclusively dispensing unused supplies to exclusively receiving used supplies.

17 Claims, 10 Drawing Sheets

CONVERTIBLE CONTAINER

FIELD

The present disclosure relates to supplies dispensing and waste disposal devices, and in particular to a convertible container for dispensing new supplies and disposing used supplies.

BACKGROUND

In the medical and other fields, devices with sharp points or edges that can puncture or cut skin are generally known as sharps. Such sharps can include needles, syringes with needles, scalpels, blades, disposable scissors, suture equipment, stylets, and trocars, broken test tubes, and glass that may contain human blood, fluids and tissues with pathogens. Most Traditional sharps containers are "disposal only" devices. There are sharps containers having a solder hinged divider that is pushed to the bottom corner of the container as the used needles get pushed through the disposal tab. However, such sharps containers do not prevent liquids from crossing the "disposal" side over to the "supply" side and vice versa. This causes a major concern when dealing with biohazardous waste.

SUMMARY

In various industries, it is desired to be able to safely carry safe supplies, such as unused syringes or other gears, in the same device as the disposal unit.

In an embodiment, the sharps container may be a handheld container having two compartments. The container can function initially as a supply carrier. The sharps container may be converted to a half supply and half disposal device by attaching a first inserts tab to the opening of the first compartment for disposal, and may be further converted to a full disposal container by attaching a second inserts tab to the opening of the second compartment for disposal.

In another embodiment, the sharps container has one or more dividers extended, in a sealed manner, from the bottom surface of the container. The dividers divide the space defined by the walls of the container into two or more compartments. Each compartment is sealed from an adjacent compartment where liquid at the bottom of the compartment cannot communicate to an adjacent compartment. The dividers can be solid ribs or plates. As such, the sharps container allows to safely carry supplies on one side of the solid rib, and their disposal waste on the other, without allowing liquids to pass through the base of the container, and thus avoid contamination of the supplies.

As such, the sharps container may be converted from a "supply carrier" to partially disposal, and to full disposal by attaching one or more inserts tabs to the openings of the one or more compartments. Unlike the containers with pendulum or swinging dividers where once the containers are full, certain area of the containers are not used, the sharps container of the present disclosure has no wasted space, and the full space of the sharps container can be used. The sharps container is safer as no liquids in the compartments can pass through the base of the container.

In an aspect, there is provided a container for dispensing and disposing supplies, comprising: a receptacle having a base and a plurality of walls extended up from the base; one or more compartments formed in the receptacle, wherein the one or more compartments is configured to be fluid-tightly sealed from each other; and one or more insert members, each configured to convert one of the one or more compartments from exclusively dispensing unused supplies to exclusively receiving used supplies.

In another aspect, the one or more insert members are configured to receive the used supplies and restricting retrieval of the used supplies.

In another aspect, each of the one or more insert members is configured to be securely mounted at an opening of one of the one or more compartments.

In another aspect, each of the one or more insert members comprises a plurality of the fingers pointing toward a central opening.

In another aspect, the container further comprises one or more dividers for dividing a space defined by the base and the plurality side walls of the container into two or more fluid-tight compartments.

In another aspect, the unused supplies are unused medical supplies or unused medical sharps, and the used supplies are used medical supplies or used medical sharps.

In another aspect, the container further comprises a lid hinged to one of the plurality of side walls for opening and closing the container.

In another aspect, each of the one or more the insert members comprises a plurality of tongues configured to be receive in a plurality of grooves on the plurality of side walls.

In another aspect, each of the plurality of grooves includes one or more extended tabs for supporting one of the one or more the insert members.

In another aspect, the container further comprises a latch for securely closing the lid.

BRIEF DESCRIPTION OF THE DRAWINGS

Reference will now be made, by way of example, to the accompanying drawings which show example embodiments of the present application, and in which.

Similar reference numerals may have been used in different figures to denote similar components.

DETAILED DESCRIPTION OF EXAMPLE EMBODIMENTS

Figure 1:
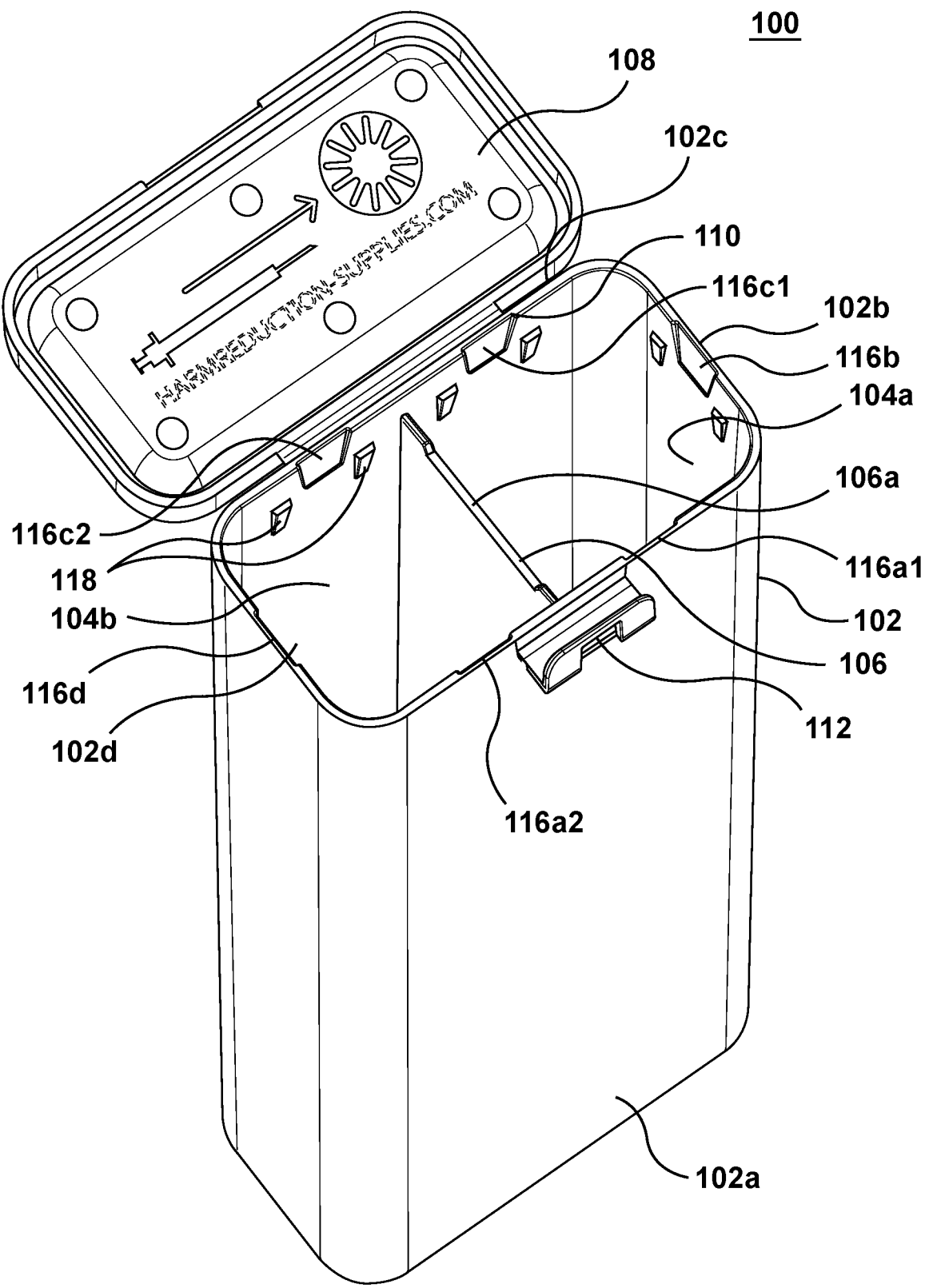
FIG. 1 is a front perspective view of a sharps container, according to an embodiment.
Figure 2:
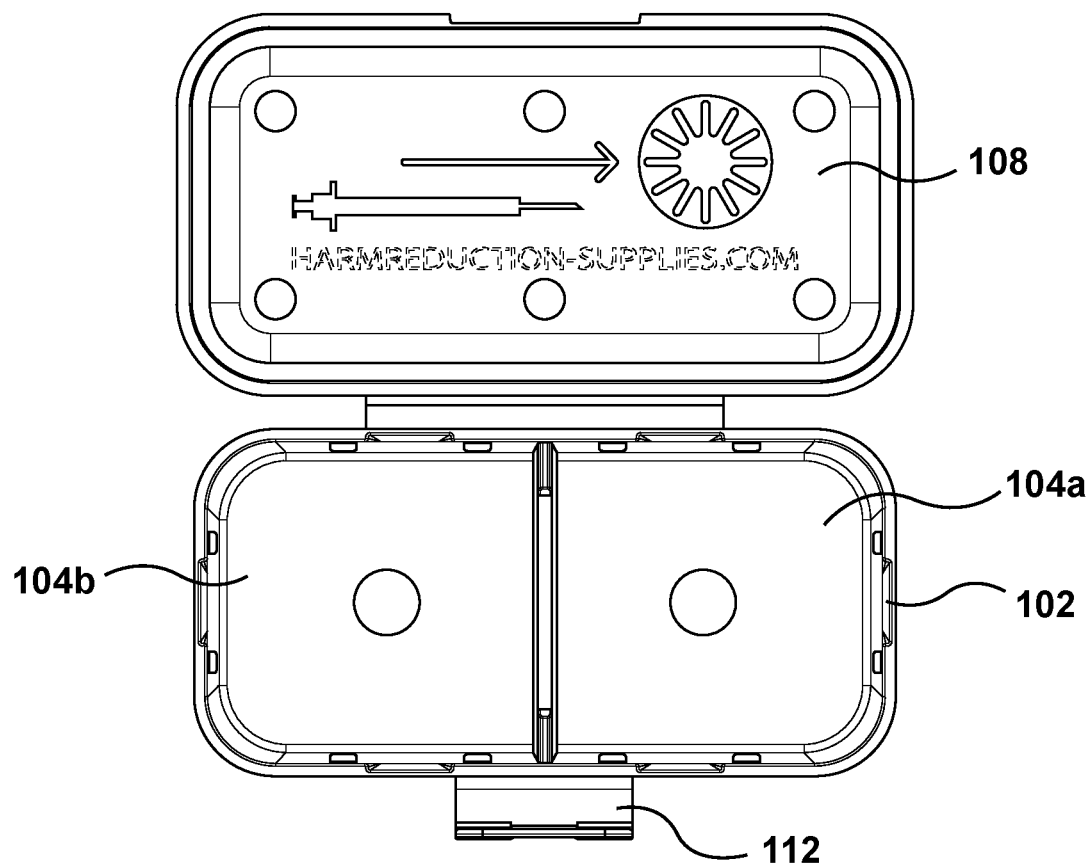
FIG. 2 is a top view of the sharps container of FIG. 1.
Figure 3:
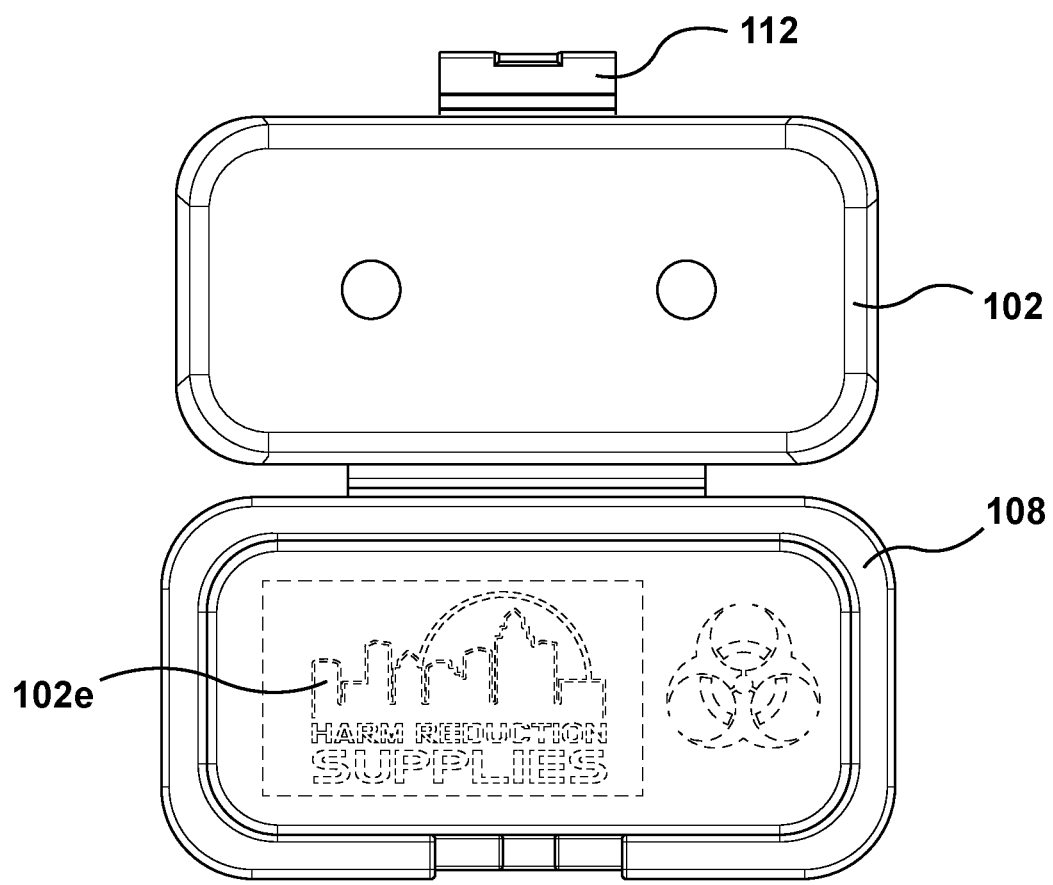
FIG. 3 is a bottom view of the sharps container of FIG. 1.
Figure 4:
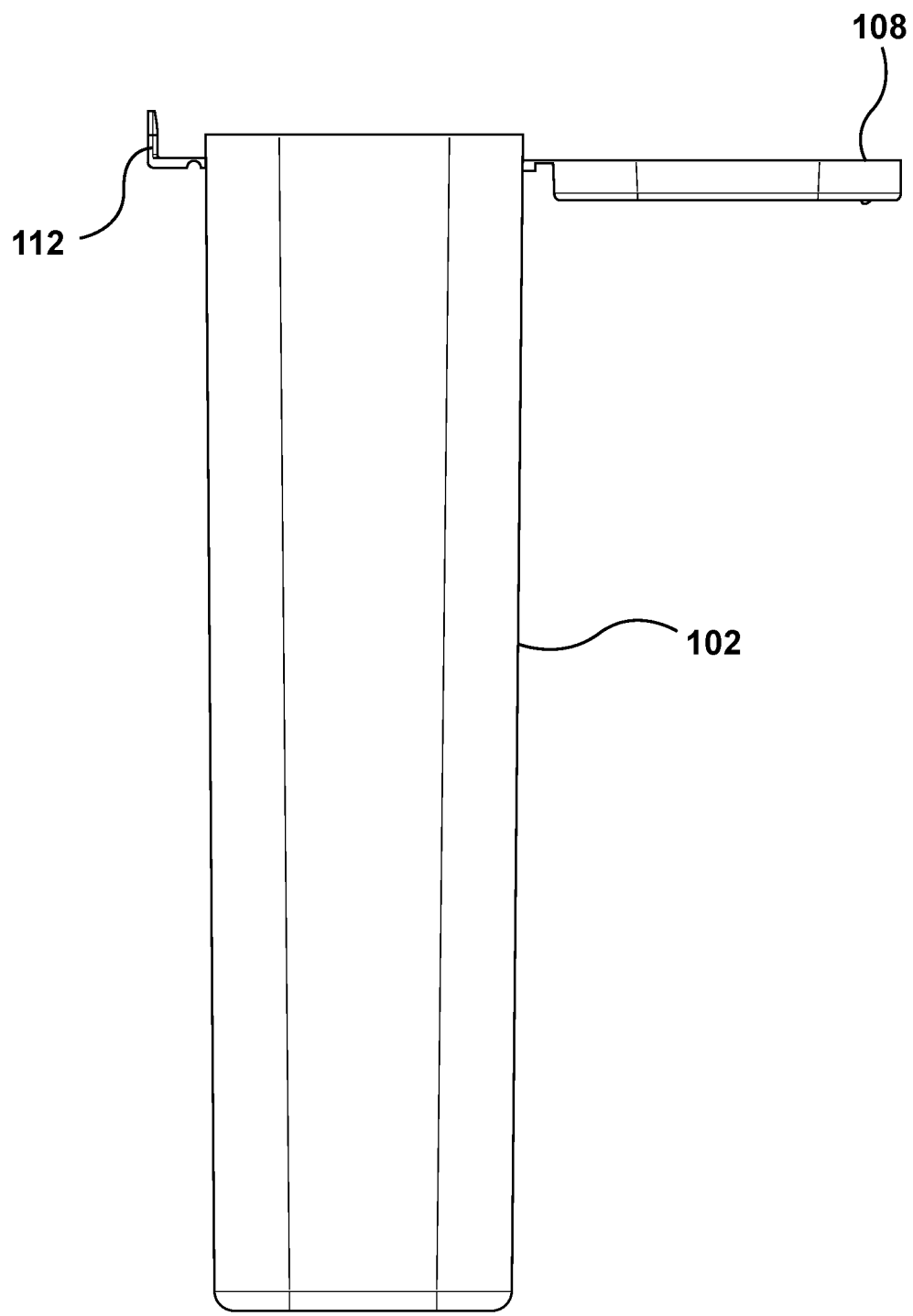
FIG. 4 is a side view of the sharps container of FIG. 1.
Figure 5:
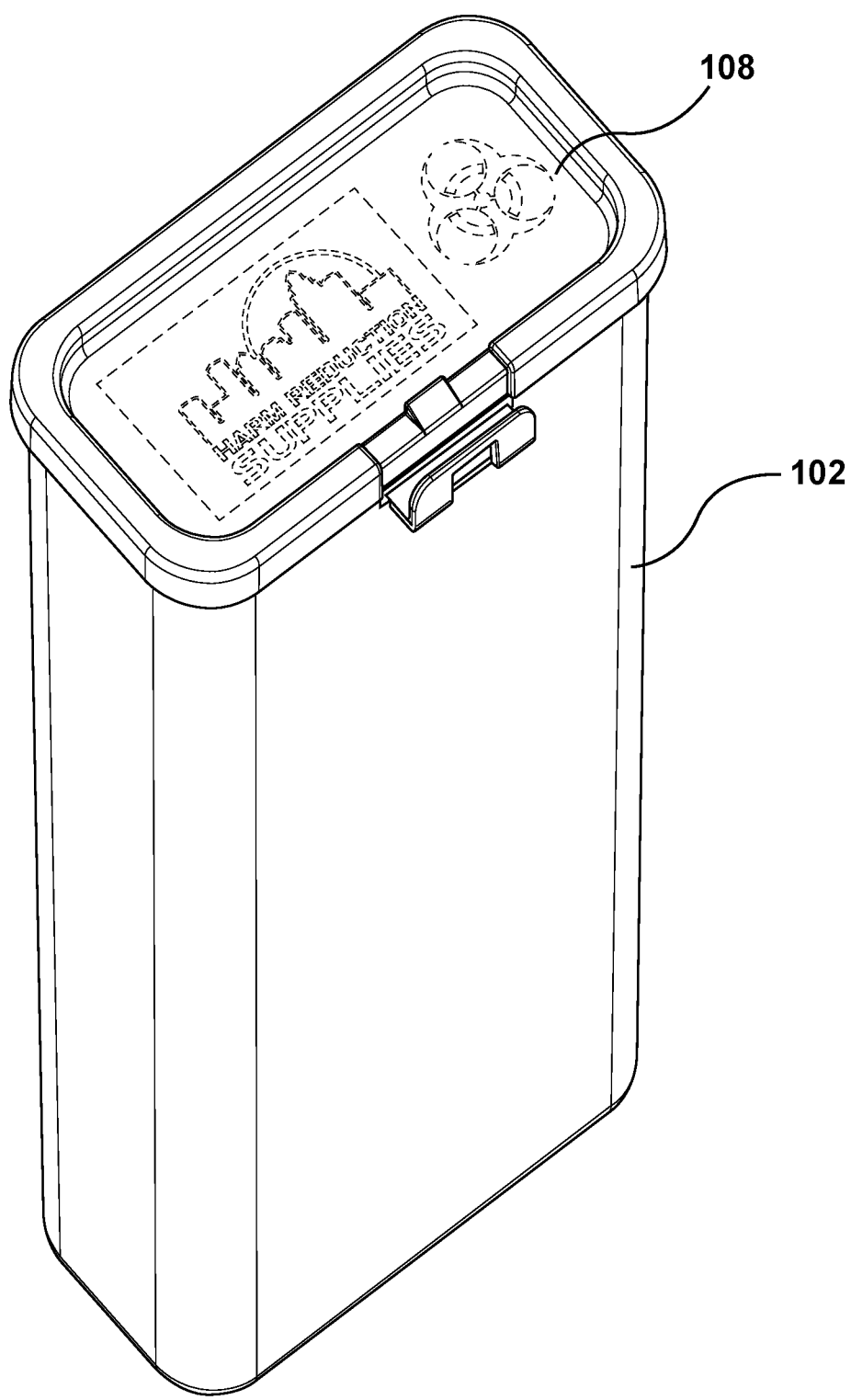
FIG. 5 is a perspective view of the sharps container of FIG. 1, with the lid closed.

FIGS. 1-5 illustrate a container 100 for dispensing and disposing supplies. The supplies may include medical sharps, syringes, hypodermic needles, disposable scalpels and blades, contaminated glass and certain plastics, guidewires used in surgery, and other disposable supplies that may be used in a clinic, pharmacy, hospital or a laboratory. The container 100 may be configured to be a handheld container. The container 100 may also have a bigger or smaller size.

The container 100 includes a receptacle 102. The receptacle 102 includes a plurality of walls defining a space for receiving unused or used supplies. In the example of FIGS. 1-5, the receptacle 102 includes side walls 102a-102d and a bottom wall or base 102e to form a fluid tight space. The receptacle 102 may be made from any suitable materials, such as plastic. The receptacle 102 may also have various shapes, such as a cylindrical, cubic, or pentagonal shape.

The receptacle 102 may include one or more dividers 106 for dividing the space formed by the walls 102a-102d into two or more compartments. The dividers 106 can be solid ribs or plates. The dividers 106 be flat or other shapes, such as a waved shape. Each compartment is separated from an adjacent compartment in a sealed manner, in which the one or more dividers 106 are configured to extend from the inner surface of the bottom wall or base 102e (FIG. 3) up along any two side walls, such as 102a and 102c, or 102b and 102d, in a liquid-tight manner, such that the liquid contained in the supplies in a compartment cannot flow to an adjacent compartment. The compartments may also have various shapes, such as a cylindrical, cubic, or pentagonal shape.

In the example of FIGS. 1-5, a divider 106 is configured to extend from the inner surface of the bottom wall 102e along the walls 102a and 102c towards the top edges of the side walls 102a and 102c. In some examples, the height of the divider 106 is lower than the top edges of the walls 102a-102d. In the example of FIGS. 1-5, the divider 106 and the walls 102a-102e define two compartments 104a and 104b.

Although FIGS. 1-5 only illustrate two compartments 104a and 104b, the receptacle 102 may include one compartment, or three or more compartments. In some examples, the receptacle 102 does not include the divider 106, and receptacle include only one compartment. The receptacle 102 may also include two or more dividers 106. In the example that the receptacle 102 includes two dividers 106, the receptacle 102 has three compartments, and two dividers 106 are formed to divide the space into three compartments. The receptacle 102 may also include three or more dividers to divide the space into four or more compartments in a sealed manner.

Each of the one or more compartments 104a and 104b is configured to be a dispensing compartment, or a disposal compartment at a time. The dispensing compartment is configured to receive exclusively unused supplies such as medical sharps or other medical supplies. A disposal compartment is configured to receive exclusively used supplies.

In the example of FIGS. 1-5, the compartments 104a and 104b are initially configured to be dispensing compartments. Each compartment 104a and 104b has an opening defined by the top edges of side walls 102a-102d and the divider 106. For example, the top edge of the divider 106, and the top edge of the side wall 102b, and top edges of side walls 102a and 102c between the divider 106 and the side wall 102b define the opening of the compartment of 104a. Similarly, the top edge of the divider 106, and the top edge of the side wall 102d, and top edges of side walls 102a and 102c between the divider 106 and the side wall 102d define the opening of the compartment of 104b.

In some examples, the container 100 may also include a lid 108 hinged to the top edge of the side wall 102c for opening and closing the opening of the container 100. As well, the container 100 may also include a latch 112 near the top edge of the side wall 102a for securing the lid 108 when the lid 108 is closed. In some examples, the lid 108 may also include a handle (not shown) on the top surface of the lid 108.

When supplies in a dispending compartment 104a or 104b are all dispensed, the dispensing compartment 104a or 104b is configured to be convertible to a disposal compartment for receiving exclusively used supplies, such as used medical sharps and supplies. In the example of FIGS. 1-5, after all the supplies have been dispensed, each compartment 104a and 104b is configured to receive an insert member 114 (FIG. 6) for covering the opening of the compartment. Once an insert member 114 covers a compartment 104a or 104b, the covered compartment 104a or 104b is converted from a dispensing compartment to a disposal compartment. In the example of FIG. 7, after the supplies in the dispending compartment 104a are dispensed, and the insert member 114 is covered to the opening of the compartment 104a, the compartment 104a is converted from a dispensing compartment to a disposal compartment for exclusively receiving used supplies.

The insert member 114 is configured to be securely mounted at the opening of each of the compartments 104a and 104b. In the example of the FIG. 6, the insert member 114 has three tongues 120a-120d extending from the edges of the insert member 114. The insert member 114 may have more or fewer tongues. The insert member 114 can be formed from any suitable material such as plastic. The insert member 114 may also have various shapes complementary to the shapes of the compartment opening to cover the opening of the compartment. The insert member 114 has a top surface 114a and a bottom surface 114b. Both the top surface 114a and bottom surface 114b can be identical.

As illustrated in the example of FIG. 1, the divider 106 has a groove 106a for receiving the tongue 120d, and the compartment 104a has corresponding grooves 116a1, 116b, 116c1 to receive the tongues 120a, 120b, 120c of the insert member 114, respectively. The compartment 104b has corresponding grooves 116d, 116c2, and 116a2, to receive the tongues 120a, 120b, 120c of the insert member 114, respectively. The insert member 114 and the compartments 104a and 104b may also have other configurations as long as the insert member 114 is securely received at the opening of the compartment 104a or 104b.

In some examples, each groove 116a1, 116a2, 116b, 116c1, 116c2, and 116d has one or more extended tabs 118 for receiving the tongues 120a, 120b, 120c of the insert member 114. In the example of FIG. 1, two tabs 118 may be located at two sides of each of the grooves 116a1, 116a2, 116b, 116c1, 116c2, and 116d. In some examples, the one or more extended tabs 118 may be close to the top edges of the walls 102a-102d and the positions of the tabs 118 may be varied. The one or more extended tabs 118 are optional and may not be included on the container 100.

Figure 6:
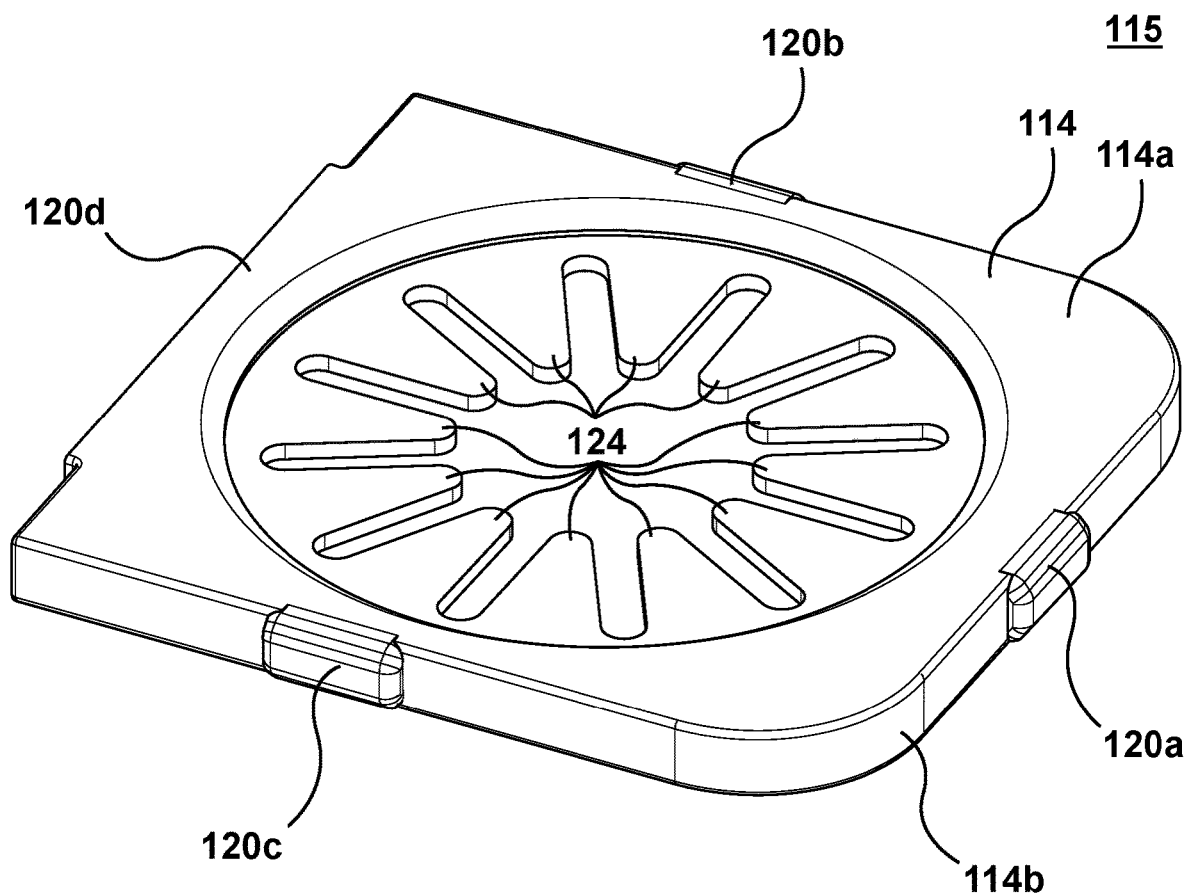
FIG. 6 is a perspective view of an insert tab, according to an embodiment.
Figure 7:
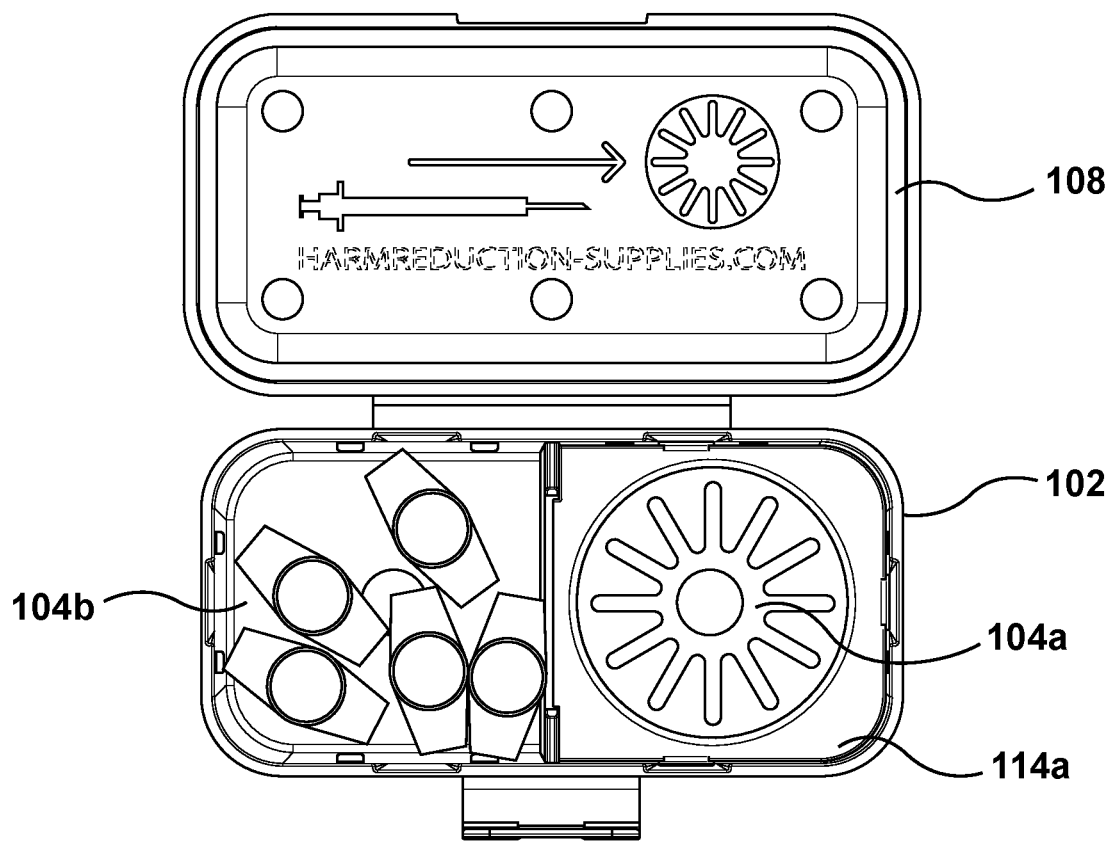
FIG. 7 is a top view of the sharps container of FIG. 1 with an insert tab placed on a compartment of the sharps container, according to another embodiment.

As illustrated in the example of FIGS. 6-10, the insert member 114 is configured such that used supplies can relatively easily pass through the insert member 114 for disposal in the disposal compartment 104a, yet relatively difficult to be retrieved from the disposal compartment 104 via the insert member 114. In the example of FIG. 6, the insert member 114 comprises a plurality of the fingers 124 pointing toward an opening substantially at the center. The free space formed by the fingers 124 allows the used supplies, such as medical sharps, to pass through the insert member 114 for disposal in the compartment 104a or 104b covered by the insert member 114. However, due to the arrangement of the fingers 124 of the insert member 114, the supplies disposed therein are relatively difficult to retrieve from the compartment via the insert member 114, as the supplies have to be oriented to the position where the space formed by the fingers 124 and the central opening allows the supplies to pass through the insert member 114 to be retrieved.

Figure 8:
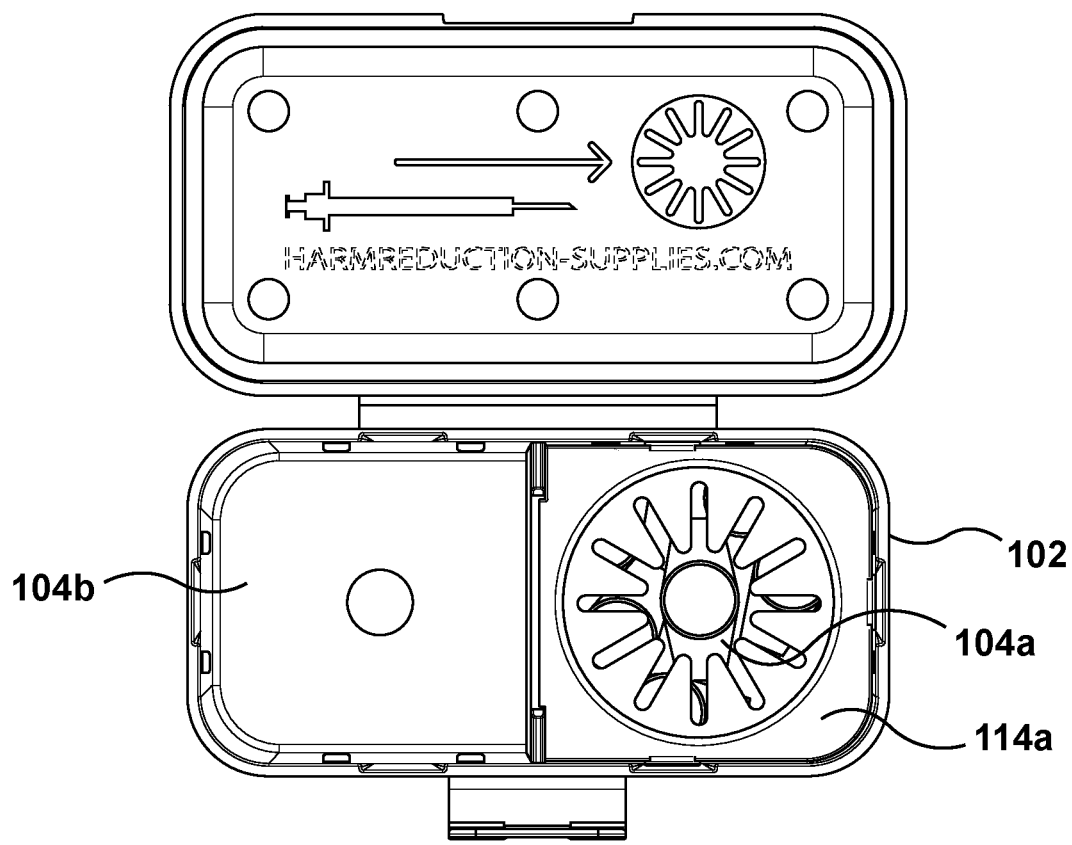
FIG. 8 is a top view of the sharps container of FIG. 7, according to another embodiment.

As illustrated in the example of FIGS. 7 and 8, after the supplies in compartment 104a are completely dispensed, the compartment 104a may be converted to a disposal compartment by attaching the insert member 114a to the opening of the compartment 104a, in the same manner as described above. As such, the space of the compartment 104a may be used to receive the used supplies for disposal.

Figure 9:
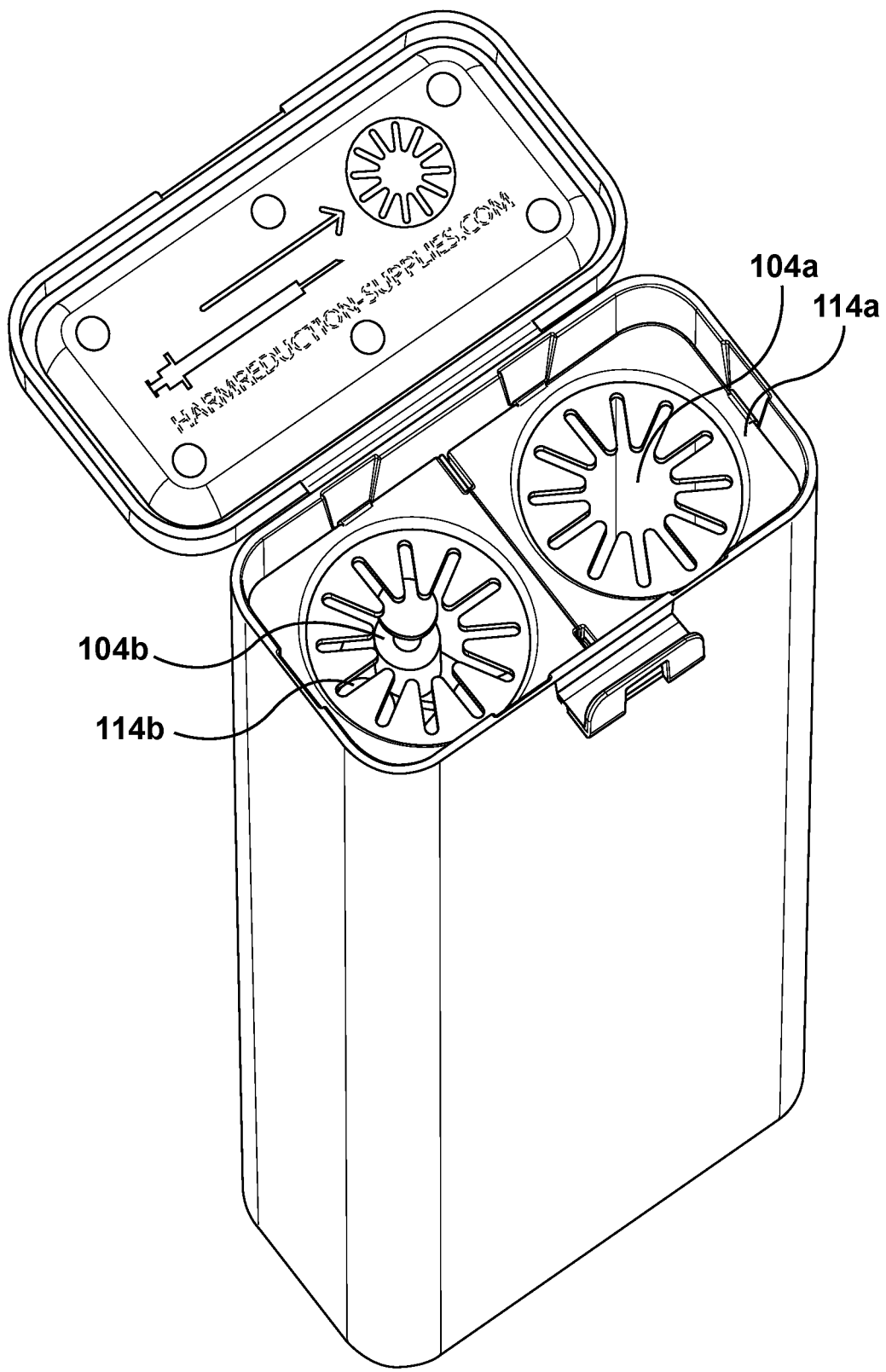
FIG. 9 is a perspective view of the sharps container of FIG. 1, with two insert tabs placed on both compartments of the sharps container, according to another embodiment.
Figure 10:
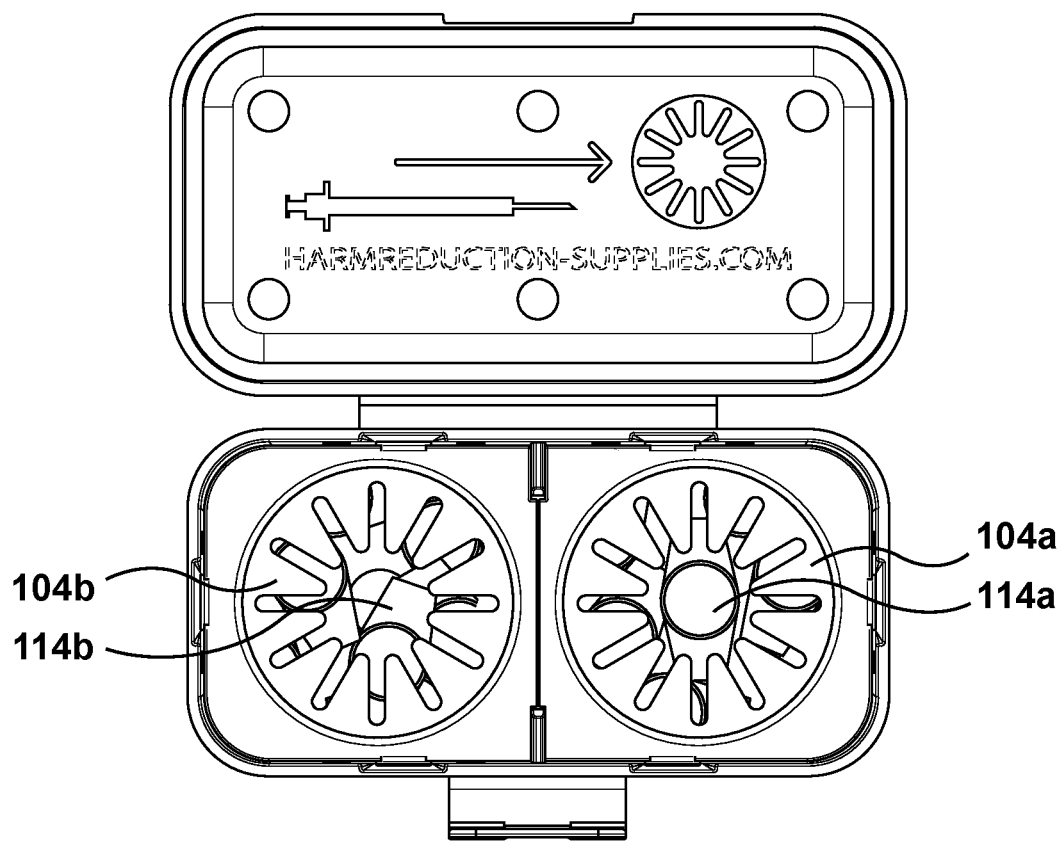
FIG. 10 is a top view of the sharps container of FIG. 9.

As illustrated in the example of FIGS. 9 and 10, after the supplies in compartment 104b are completely dispensed, the compartment 104b may be converted to a second disposal compartment by attaching the insert member 114b to the opening of the compartment 104b, in the same manner as converting compartment 104 from a dispensing compartment to a disposal compartment, as described above. As such, the space of the compartment 104b may be used to receive the used supplies for disposal. As such, all the compartments 104a and 104b can be converted from supplies dispensing compartments to disposal compartments to receive used supplies by attaching the insert members 114a and 114b to the openings of the compartments 104a and 104b.

The container 100 may also include one, three or more compartments initially for dispensing supplies. After the supplies in each compartment are completely dispensed, the compartment can be converted to a dispensing compartment by attaching an insert member 114 to the opening of the compartment.

In use, a user may load unused supplies in all of the compartments 104a and 104b of the container 100. When the supplies are fully dispensed in a compartment and the compartment is empty, the user may securely place an insert member to the opening of the compartment to convert the compartment to a disposal compartment. For example, after the supplies in compartment 104a are fully dispensed and the compartment 104a is empty, the user may place an insert member 114a to the opening of the compartment 104a by pressing the tongues 120a, 120b, 120c of the insert member 114a into respective grooves 116a1, 116b, 116c1 of compartment 104a to cover the opening of the compartment 104a. As such, the compartment 104a is converted from a dispensing compartment to a disposal compartment. The user may dispose used supplies, through the insert member, in the disposal compartment, such as compartment 104a, until the disposal compartment is substantially full or full. Similarly, when the unused supplies are fully dispensed in compartment 104b, after the user places another insert member, such as insert member 114b, to cover the opening of the compartment 104b, the compartment 104b is converted from a dispending compartment to a disposal compartment 104b. The disposal compartment 104b may then receive used supplies for disposal until the compartment is substantially full or full. As such, the space of the container 100 is fully used at all times, without wasted space.

Certain adaptations and modifications of the described embodiments can be made. Therefore, the above discussed embodiments are considered to be illustrative and not restrictive.

What is claimed is:

1. A container for dispensing and disposing supplies, comprising:
   a receptacle having a base and a plurality of side walls extended up from the base;
   one or more compartments formed in the receptacle, wherein the one or more compartments are configured to be fluid-tightly sealed from each other; and
   one or more insert members, each insert member configured to convert one of the one or more compartments from exclusively dispensing unused supplies to exclusively receiving used supplies,
   wherein each of the one or more insert members comprises a plurality of tongues configured to be received in a plurality of grooves on the plurality of side walls.

2. The container of claim 1, wherein the one or more insert members are configured to receive the used supplies and restricting retrieval of the used supplies.

3. The container of claim 1, wherein each of the one or more insert members is configured to be securely mounted at an opening of one of the one or more compartments.

4. The container of claim 1, wherein each of the one or more insert members comprises a plurality of fingers pointing toward a central opening.

5. The container of claim 1, further comprising one or more dividers for dividing a space defined by the base and the plurality of side walls of the container into two or more fluid-tight compartments.

6. The container of claim 1, wherein the unused supplies are unused medical supplies or unused medical sharps, and the used supplies are used medical supplies or used medical sharps.

7. The container of claim 1, further comprising a lid hinged to one of the plurality of side walls for opening and closing the container.

8. The container of claim 1, wherein each of the plurality of grooves includes one or more extended tabs for supporting one of the one or more the insert members.

9. The container of claim 7, further comprising a latch for securely closing the lid.

10. A container for dispensing and disposing supplies, comprising:
    a receptacle having a base and a plurality of side walls extended up from the base;
    one or more compartments formed in the receptacle, wherein the one or more compartments are configured to be fluid-tightly sealed from each other;
    one or more insert members, each insert member configured to convert one of the one or more compartments from exclusively dispensing unused supplies to exclusively receiving used supplies;
    a lid hinged to one of the plurality of side walls for opening and closing the container; and
    a latch for securely closing the lid.

11. The container of claim 10, wherein the one or more insert members are configured to receive the used supplies and restricting retrieval of the used supplies.

12. The container of claim 10, wherein each of the one or more insert members is configured to be securely mounted at an opening of one of the one or more compartments.

13. The container of claim 10, wherein each of the one or more insert members comprises a plurality of fingers pointing toward a central opening.

14. The container of claim 10, further comprising one or more dividers for dividing a space defined by the base and the plurality of side walls of the container into two or more fluid-tight compartments.

15. The container of claim 10, wherein the unused supplies are unused medical supplies or unused medical sharps, and the used supplies are used medical supplies or used medical sharps.

16. The container of claim 10, wherein each of the one or more insert members comprises a plurality of tongues configured to be received in a plurality of grooves on the plurality of side walls.

17. The container of claim 16, wherein each of the plurality of grooves includes one or more extended tabs for supporting one of the one or more the insert members.

* * * * *